United States Patent

Kojima et al.

[11] Patent Number: 5,882,672
[45] Date of Patent: Mar. 16, 1999

[54] CRUDE DRUG-CONTAINING FEED

[75] Inventors: Yasuhiko Kojima; Tooru Takahashi, both of Kanagawa, Japan

[73] Assignee: Yamanouchi Pharmaceutical Co., Ltd., Tokyo, Japan

[21] Appl. No.: 765,125
[22] PCT Filed: Jun. 14, 1995
[86] PCT No.: PCT/JP95/01186
  § 371 Date: Dec. 5, 1996
  § 102(e) Date: Dec. 5, 1996
[87] PCT Pub. No.: WO95/34218
  PCT Pub. Date: Dec. 21, 1995

[30] Foreign Application Priority Data

Jun. 16, 1994 [JP] Japan .................................. 6-158054

[51] Int. Cl.$^6$ ........................................... A61K 35/78
[52] U.S. Cl. .................................... 424/438; 424/442
[58] Field of Search .................................. 424/438, 442

[56] References Cited

U.S. PATENT DOCUMENTS 5,464,618  11/1995  Doane et al. .................... 424/195.1

FOREIGN PATENT DOCUMENTS 0424534   5/1991   European Pat. Off. .
61-119144  6/1986   Japan .
1172339   7/1989   Japan .

OTHER PUBLICATIONS

British Journal of Nutrition vol. 66 No. 2 (1991) pp. 331–349.
Leng–Peschlow, E. "Plantago ovata seeds as dietary fibre supplement: physiological and metabolic effects in rats".
Nutrition Reports International vol. 27 No. 4 (1983) pp. 681–687.
Lina, S., et al. "Evaluation Of The Protein Quality Of Food Mixes In Albino Rats".
J. Agric. Food Chem. vol. 28 No. 2 (1980) pp. 364–366 Dreher, M., et al. "Cucurbit Seed Coat Composition".
Poultry Science vol. 66 No. 8 (1987) pp. 1372–1378 Douglas, J.H., et al. "Buffalo Gourd Seed in Broiler Starter Rations Under Different Dietary Regimens".
British J. of Nutrition (1991) 66–331–349 Leng–Peschlow.
J. Agric. Food. Chem. 1980, 26, 364–366 Dreher et al.

*Primary Examiner*—Peter F. Kulkosky
*Attorney, Agent, or Firm*—Burgess, Ryan & Wayne

[57] ABSTRACT

A mixed feed or a feed additive, which comprises Cucurbita Seed, Plantago and Lornicera.

Other crude drugs such as Safflower, Licorice, Mabiacao, Pugongying, Houttuynia and Juhua may be compounded in addition to the above crude drugs.

For breeding cattle, swine, fowl, Hamachi, and the like, the above-described mixed feed, or the feed additive compounded with the marketed feed may be used.

The resistance to diseases of the fed animals is improved, healthy candicidin can be maintained during the breeding, and the meat quality, egg quality, or the like is improved.

3 Claims, 1 Drawing Sheet

CRUDE DRUG-CONTAINING FEED

RELATED APPLICATIONS

This application is a 371 application of PCT/JP95/01186 filed Jun. 14, 1995.

BACKGROUND OF THE INVENTION

1) Field of the Industrial Use

This invention relates to a feed for increasing the disease resistance of domestic animals, domestic fowls and fishes and improving their qualities such as the meat quality, egg quality, and the like.

2) Prior Art

Most of the prior art assorted feed and mixed feed have been produced with the aim of supplying domestic animals, domestic, fowl, fish, and the like with nutritive substances which can maintain their growth conditions within economically acceptable range in the usual natural environment. The purpose of their production was to allow animals to spend days in good conditions during a period until they can be shipped economically, rather than to maintain their length of life as long as possible under healthy conditions. That is, the main purpose was to improve body weight gain, feed requiring ratio, and the like during a period prior to their shipping. With regard to diseases of these animals, vaccines have been used for the prevention of diseases and antibiotics and antimicrobial agents have been used for the treatment of diseases.

In recent years, however, the appearance of resistant bacteria and residual antibiotics in meat and eggs became social problems, which resulted in the legal restriction of the use of antibiotics, antimicrobial agents, and the like and frequent strict inspections for this purpose. That is, shipping of animals has been banned not only during the use of these drugs but also for a certain period after their use. In addition, environmental deterioration caused by dense rearing, and the like in quest of profitability has resulted in the increase of intractable diseases, so-called opportunistic infections, and the like, which has accelerated reduction of productivity and profitability.

Taking such circumstances into consideration, the inventors of the present invention have conducted studies on the improvement of the rearing environment for all types of domestic animals, domestic fowl, cultured fish, and the like, so that their health can be maintained through the prevention of their infection with viruses, bacteria and parasites without using drugs for animals (antibiotics and antimicrobial agents) as far as possible and their meat quality, egg quality, milk quality, and the like can be improved. As a result, the present inventors found that the blending of certain crude drugs with feeds for domestic animals, domestic fowl, cultured fish, and the like can increase the resistance of these animals against viruses, bacteria and parasites and improve the meat and egg qualities, and accomplished the present invention.

Accordingly, the object of the present invention is to maintain the health of domestic animals, domestic fowl, cultured fish, and the like without using antibiotics and antimicrobial agents as far as possible.

SUMMARY OF THE INVENTION

In order to achieve such an object, the present inventors have scientifically examined various crude drugs having various biological activities and found that the disease resistance of domestic animals, cultured animals, and the like can be increased markedly and the meat quality, egg quality, and the like can be improved, when at least one crude drug selected from the group consisting of Cucurbita Seed, Plantago and Lonicera is added to a feed.

DESCRIPTION OF THE PREFERRED EMBODIMENTS

Figure 1:
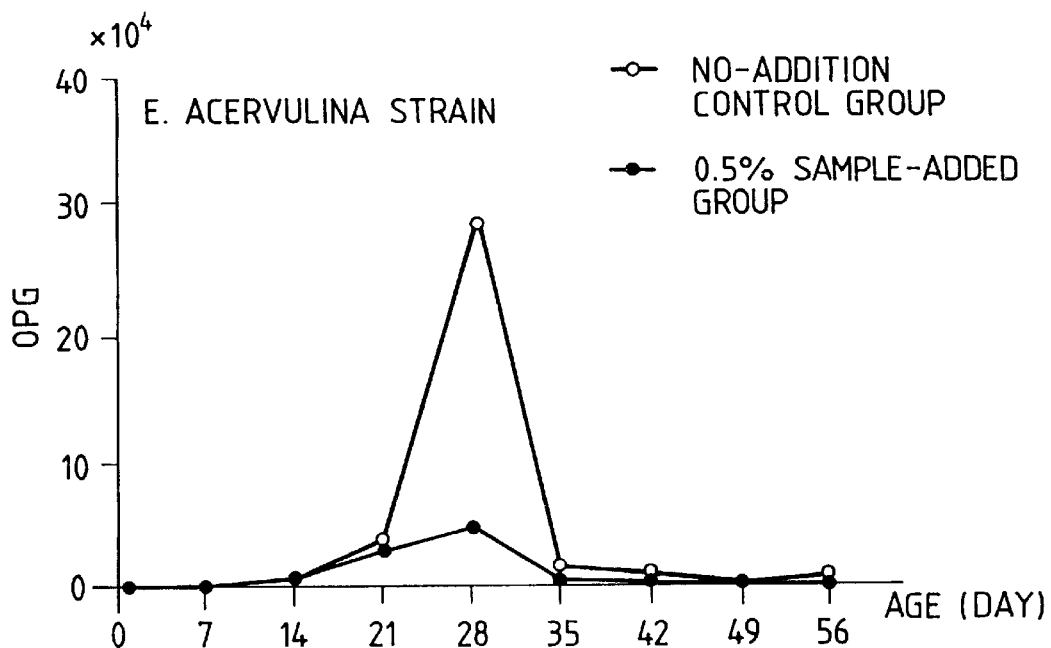
FIG. 1 is a graph showing the result of the oocyst excretion (OPG) (*E. acervulina*) in broiler coccidium test carried out in Example 1.

Accordingly, the present invention relates to a feed which comprises at least one crude drug selected from the group consisting of Cucurbita Seed, Plantago and Lonicera. The present invention includes those comprising one, two or three of these crude drugs and, in particular, relates to a feed comprising these three crude drugs.

The present invention also relates to a feed which comprises at least one crude drug (in particular, all three crude drugs) selected from the group consisting of Cucurbita Seed, Plantago and Lonicera and at least one crude drug selected from the group consisting of Safflower, Licorice, Mabiacao, Pugongying, Houttuynia and Juhua.

Feed additives are also included in the feed of the present invention.

First, crude drugs used in the present invention are described.

Cucurbita Seed (*Cucurbita moschata* Duch.) is the seed of a plant belonging to the family Cucurbitaceae. Though Cucurbita Seed can be used as raw seeds, a dried preparation may be desirable in view of the preservation of the feed. Seed coats alone may also be used. As the components, Cucurbita Seed contains cucurbitin, proteins and vitamins A, $B_1$, $B_2$ and C, as well as carotene, and the like.

Plantago (*Plantago asiatica* L.) is a plant belonging to the family Plantaginaceae and is used as its mature seeds (Plantaginis Semen) or whole plant (Plantaginis Herba). As the components, Plantago contains polysaccharides, plant-enolic acid, succinic acid, adenine, aucubin, plantaginin, vitamins A and $B_1$, and the like. As the crude drug, it is used in human as an anti-inflammatory agent, a diuretic agent and an antidiarrhoic agent.

Lonicera (*Lonicera japonica* THUNB.) is a plant belonging to the family Caprifoliaceae and is used as its flowers or buds (Jinyinhua or lonicerae flos) or leaves, stems or whole plant (Rendongteng or lenicerae flos and caulis). As the components, Lonicera includes a wax-like substance, inositol, tannin, saponin, lonicerin, and the like. As the crude drug, it is used as an antipyretic agent, a detoxicating agent, a diuretic agent and an anti-inflammatory agent.

The present inventors have found that certain plants belonging to the family Cucurbitaceae, such as Cucurbita Seed, can induce interferon and obtained a patent (U.S. Pat. No. 4,421,746).

The present inventors also have reported the IgE antibody production-inhibiting effect and mitogen activity of Cucurbita Seed, and the like at the 43th meeting of the Japanese Society of Allergology.

In addition, the present inventors have found that Plantago and Lonicera can induce interferon and obtained a patent (U.S. Pat. No. 4,469,685).

Although it has been proposed that a total of 43 Chinese herbal crude drugs (Kampo) can be used for the prevention or treatment of animal diseases (unexamined published Japanese patent application (Kokai) No. 1-172341), it does not disclose the use of the crude drugs of the present invention. In addition, nothing has been reported on the effects of their use to increase the resistance against a broad range of microorganisms, parasites, and the like in all types of domestic animals, domestic fowl, cultured fish, and the like and to improve the meat quality and egg quality of these animals.

Next, the other crude drugs to be blended as optional components in the present invention will be described.

Safflower (*Carthamus tinctorius* L.) is a dried preparation of tubulous flowers of a plant belonging to the family Asteraceae. As the components, it contains carthamin, safloryellow, lignan and sterol. It is used for the treatment of hematogenous disturbances such as gynecological disorders, cold oversensitiveness, climacteric disturbance, and the like.

The present inventors have also obtained a patent (U.S. Pat. No. 4,456,597) regarding a method for the inducing interferon by Safflower.

Licorice (*Glycyrrhiza uralensis*) is a dried preparation of roots and stolons of a plant belonging to the family Leguminosae. Its main component is glycyrrhizin. Licorice is used as an emollient, a remission agent, an antitussive agent, a sedative agent and an expectorant.

Mabiancao (*Vervena officinalis* L.) is a dried preparation of the whole plant body, including roots, of a plant belonging to the family Vervenaceae. Its components include a monoterpene glycoside. It is used as an anti-inflammatory and analgesic agent, a hemostatic agent, an antimicrobial agent, a hydragogue and an emmenagogue.

Pugongying (*Taraxacum mongolicum*) is a dried preparation of the whole plant body, including roots, of a plant belonging to the family Asteraceae. As the components, Pugongying contains sterols, inulin and pectin. It is used as an antipyretic agent, an anti-inflammatory agent, a stomachic agent, a diuretic agent and a galactagogue.

Houttuynia (*Houttuynia cordata* Thunb.) is the whole plant body, including roots, of a plant belonging to the family Saururaceae. It contains odorous components such as decanoyl acetoaldehyde, lauric aldehyde, methyl-n-nonyl ketone, capric aldehyde, 3-ketodecanal, methyllauryl sulfide, myrcene, flavonoid, and the like. It is used as a folk decoction medicine for the treatment of constipation, cold syndrome, empyema, and the like and as an external use medicine for the treatment of hemorrhoids, tumors, low back pain, cold oversensitiveness, and the like.

Juhua (*Chrysanthemum lavandulaefolium* Makino) is a dried preparation of capitula of a plant belonging to the family Asteraceae. As the components, Juhua contains 2,2, 4-trimethyl-3-cyclohexynelcarboxylic acid, acacetin-7-rhamnoglucoside, apigeninglucoside, adenine, choline, carbohydrates, and the like. It is used as an antipyretic agent, a detoxicating agent, a sedative agent and an anti-inflammatory agent.

In China, the following three methods have been reported on the use of crude drugs as feed additives [Chikusannokenkyu (*Studies on Animal Husbandry*), Vol. 48, No. 1, pp. 9–12 (1994)].

(1) A method in which a crude drug is used as a single ingredient.

(2) A method in which 1 or 2 main plants are mixed with 2 to 6 auxiliary crude drugs, and used.

(3) A method in which crude drugs as the main ingredients are mixed with necessary Western drugs (minerals, amino acids, and the like) and used as a Chinese-Western combined additive.

They are used in swines, domestic fowl and ruminants by the following methods.

(1) Swine

Artemisia Herb is blended with an assorted feed in an amount of 2%, and the blend is further mixed with Paulownia Leaf, Pinus Leaf, Leonurus, Juanbai, Sophorae Radix, Oufurugyo, Atractylodes Lancea Rhizome, and the like.

(2) Domestic fowl

Buguzhi, Leonurus, Luole, Astragalus Root, Heshouwu, Zingyoku, Malt, Suanzaoren, Baibiandou, Puerariae Radix, Codonopsis Rhizoma, Wumei, Baizhu, Orange Peel, Angelicae Radix, Atractylodis Rhizoma, Cnidium Rhizoma, Dioscoreae Radix, Guya, Nüzhenzi, Epimedium, Yemugua, Fluorite, Hakutoo-oo, Kengyoku, Lajiao, and the like are added.

(3) Ruminants

It has been reported that certain crude drugs such as Pinus Needle, Hoelen, Akebia Stem, Malva Seed, Tongcao, and the like were effective in improving the disease resistance and animal qualities.

Such crude drugs, however, are not used in the present invention.

According to the present invention, the particular crude drugs described in the foregoing may be used as raw powders or water or organic solvent extracts. That is, they are used as raw powders, solution preparations, powder preparations, formed preparations, percolating preparations, and the like. Methanol, ethanol, acetone, and the like may be used as the organic solvent. These organic solvents may be used by mixing with water or two or more organic solvents. Extraction may be carried out by adding several volumes of solvent to the crude drugs and extracting or percolating the drugs at ordinary temperature or with heating. When used as raw powders, fresh, shade-dried or dried crude drugs are shredded or powdered. In that case, they may be mixed with components commonly used in the drug preparation and used as powder or granule preparations. In general, a raw powder is used after its drying and pulverization. If necessary, a pellet or a drinking water form can be prepared from the powder and may be used.

When mixed with a common feed or assorted feed, the aforementioned powders or extracts of these crude drugs may be added thereto. The common feed or assorted feed may be either a homemade feed or a commercial feed. The amount to be added may preferably be in the range of from 0.05 to 5% by weight based on the feed. The amount if smaller than this range would reduce the effects of the crude drug and if larger than this range would cause a disadvantage in view of the palatability of domestic animals, and the like and the economy. In addition, these crude drugs may be added to a feed directly or after mixing them with vitamins, minerals such as montmorillonite, defatted rice bran, and, the like.

Examples of domestic animals, domestic fowl and fish to which the crude drug components of the present invention can be administered include domestic animals such as swine, milking cows, beef cattle, and the like, domestic fowl such as broilers, layers, quails, and the like and cultured fish such as yellowtail (*Seriola quinqueradiata*), Hamachi (young yellowtail), eels, sea breams, and the like.

According to the present invention, Cucurbita Seed, Plantago and Lonicera can be used alone, but combined use of the three crude drugs will further improve their effects. Such effects can be improved more strongly when these crude drugs are blended with at least one of the aforementioned Safflower, Licorice, Mabiacao, Pugongying, Houttuynia and Juhua depending on the animal to be fed.

For example, it is preferable for domestic fowl layers to blend a feed with Cucurbita Seed, Plantago, Lonicera and Safflower Powder.

For broilers, it is preferable to blend a feed with Cucurbita Seed, Plantago, Lonicera and Mabiancao Powder.

For swine, it is preferable to blend a feed with Cucurbita Seed, Plantago, Lonicera and Houttuynia Powder, and it is preferable for cattle to blend a feed with Cucurbita Seed, Plantago, Lonicera and Pugongying.

For cultured fish, it is preferable to use powders of Juhua and Licorice mixed with Cucurbita Seed, Plantago and Lonicera.

In this manner, the resistance of domestic animals, domestic fowl, fish, and the like against diseases can be increased considerably, so that their diseases which cause economical loss can be prevented and they can spend their rearing period in good conditions. At the same time, meat quality, egg quality, milk quality, and the like of domestic animals, domestic fowl and fish can be improved so that the products are free from fishy tastes and become delicious.

The following examples are provided to illustrate the present invention.

EXAMPLE 1

Early stage and late stage feeds for broiler use (SDB No. 1 and No. 2, Nippon Formula Feed Mfg. Co., Ltd.) having no antimicrobial substance such as coccidiostats, and the like were used as commercial feeds. These feeds are blends of corn, Hokuyo (northern sea) meal, soybean oil cake, purified beef tallow powder, wheat flour, alfalfa meal, vitamins, minerals, and the like, containing general components having the following analytical data.

|  | SDB No.1 | SDB No.2 |
|---|---|---|
| Crude Protein | 23.8% | 20.0% |
| Crude Fat | 5.8% | 6.8% |
| Crude Fiber | 2.5% | 2.6% |
| Crude Ash | 5.2% | 5.0% |
| Calcium | 1.04% | 1.02% |
| Phosphorus | 0.73% | 0.73% |
| GE (Cal/100 g) | 414* | 413* |
| ME (Cal/100 g) | 307* | 316* |

The term "%" means weight %, the same shall apply hereinafter.
*Calculated value Separately, a feed was prepared by mixing 1.0 kg of Cucurbita Seed Coat Powder, 0.5 kg of Plantago Seed Powder, 0.5 kg of Lonicera Flower Bud Powder and 0.3 kg of Mabiancao Powder with 0.2 kg of a montmorillonite-based mineral and 7.5 kg of defatted rice bran.

This mixed feed in an amount of 0.5% based on the feed was added to the aforementioned feed to prepare test feed.

Animal tests were carried out using a non-addition control group in which the feed containing none of these crude drugs was used for the sake of comparison (group 1) and the test feed group (group 2). In each group, a total of 300 one-day-old chicks of a broiler breed, Chanky, were used by a floor pen method, each pen containing 50 chicks (25 each for males and females). Separately, 36 individuals infected with coccidium wild strains *E. acervulina* (attenuated strain) and *E. tenella* (virulent strain) were used as seeder birds. Observation was made for 8 weeks, and the tests shown in Table 1 were carried out each week. The rearing results are shown in Table 2.

(1) Body weight gain

As shown in Table 2, the body weight gain of the group 2 was significantly higher than in the group 1 ($p<0.25$ to $p<0.01$) when they were 56 days old.

(2) Feed requiring ratio (total feed uptake/total body weight)

In the same manner, significant ($p<0.05$) improvement with a value of 91 was found in the group 2.

(3) Clinical symptoms

Dead chicks were 11 in the group 1 and 5 in the group 2, thus showing less death in the test feed group. In each case, a coccidium-caused change to a medium morbid state was found in the small intestines and caecum. Bloody stool was not found in both groups until 21 days old. However, in the group 1, bloody stool was found during 24 to 30 days with a peak on 28 days and again slight bloody stool was found after 55 days, with a total of 50 bloody stool chicks. On the contrary, in the test feed-added group 2, slight bloody stool was found in only a total of 6 chicks of 25 to 28 days age, which is significantly low ($p<0.01$).

(4) OPG measurement (oocyst numbers/g)

Figure 2:
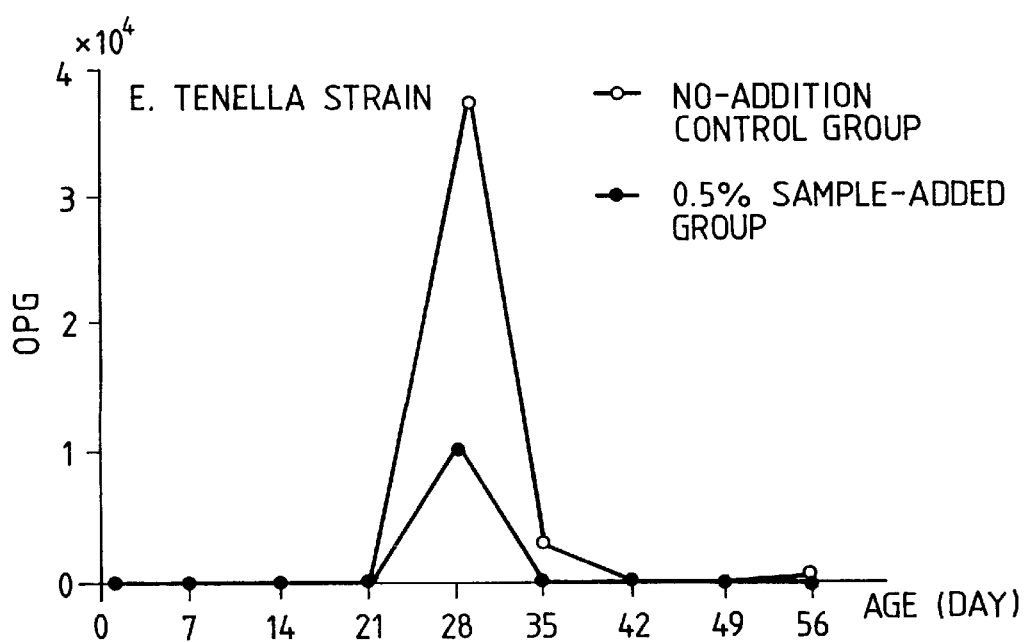
FIG. 2 is a graph showing the result of the oocyst excretion (OPG) (*E. tenella*) in broiler coccidium test carried out in Example 1.

As shown in FIGS. 1 and 2, excretion of oocysts in the group 1 was 6.7 times higher in small types and 3.4 times higher in medium types in comparison with the group 2. In and after 42 days of rearing, slight oocyst excretion was found in the group 1, but not in the group 2. A significant difference ($p<0.05$) was observed between both groups.

(5) Changes to morbid states in the bowels

In both groups, no changes to morbid states were found in the upper and central portions of the small intestines and scattered foci were found in the duodenum, but the number of foci in the group 2 was less than half in comparison with the group 1. Several petechial bleeding spots on the caecum wall were found in the group 1, but hardly recognizable in the group 2.

(6) Numbers of indigenous bacteria

When Lactobacillus and *Clostridium perfrigens* were isolated as indigenous bacteria from the small intestines and the caecum, respectively, and their numbers were counted, both groups showed no difference in the Lactobacillus counts, and the number of Clostridium colonies was slightly small in the group 2 but with no significant difference.

(7) Measurement of fat weight in the abdominal cavity

No difference was found between the two groups.

TABLE 1

| Schedule for coccidium infection test of broilers | | | | | | | | | |
|---|---|---|---|---|---|---|---|---|---|
| Age in weeks | 0 | 1 | 2 | 3 | 4 | 5 | 6 | 7 | 8 |
| Penning of chicks | ○ | | | | | | | | |
| Seeder bird infection | | | ○ | ↑ (seeder birds, oocyst excretion) | | | | | |
| Feed change | | | | ○ | | | | | |
| Body weight (each pen) | | | ○ | | ○ | ○ | ○ | | ○ |
| Feed (each pen) | | | ○ | | ○ | ○ | ○ | | ○ |
| OPG measurement (each pen) | ○ | ○ | ○ | ○ | ○ | ○ | ○ | ○ | ○ |
| Bloody stool observation (each pen) | | | | ○ | ○ | ○ | ○ | ○ | ○ |
| Anatomic inspection (10 chicks in each pen) | | | | | ○ | | | | ○ |
| Isolation of bacteria from dissected chicks (*Lactobacillus, Clostridium*) | | | | | ○ | | | | ○ |
| Measurement of fat weight in abdominal cavity | | | | | ○ | | | | ○ |

(Note) ○: performed

TEST EXAMPLE 1

Test Method
1) Infection of seeder birds and test procedure

Each of 6 one-week-old seeder birds in one pen (total 36 birds) was inoculated orally with a mixture of $1\times10^4$ *E. acervulina* mature oocysts and $1\times10^2$ *E. tenella* mature oocysts. The infection by seeder birds was carried out in accordance with the method of Brewer et al. (1970) [Brewer et al., (1970); *Exp. Parasitol.*, 28, 64–71 (1970)]. The coccidium-infected 6 chicks (seeder birds) were put in a rearing box equipped with a wire gauze floor, and the box was suspended over each pen containing 50 uninfected chicks. Excretion of oocysts by the infection source chicks started 6 to 7 days later, and the test chicks (uninfected chicks) placed under the box were infected after ingesting the oocysts.

EXAMPLE 3

Using a crude drug dried powder-blended feed prepared in the same manner as described in Example 1, a Salmonella infection protection test was carried out in accordance with the procedure of Example 2. Broiler chicks (43 days age, 14 days before shipping) were divided into 4 groups, each group including 6 chicks. A $10^{8.3}$ CFU/ml portion of a *S. typhimurium* strain 9-22-4 was inoculated by forced oral administration to carry out the infection protection test.

The test schedule is the same as shown in Table 3. The observation was conducted for 7 days after the infection. The test results were the same as those of Example 2.

TABLE 2

Summary of rearing results in coccidium infection test of broilers

Summary of rearing results

| Test Group | 1 Day Old | | 56 Days Old | | Total Weight Gain (kg) | Total Feed Intake (kg) | Feed Requiring Ratio | Rate of Raising (%) | P.S. |
| --- | --- | --- | --- | --- | --- | --- | --- | --- | --- |
| | Number of Chicks | Total Weight (kg) | Number of Chicks | Total Weight (kg) | | | | | |
| Group 1 Non-administration Control Group | 150 | 5.47 | 105 | 299.69 (100) | 294.22 (100) | 789.5 (100) | 2.68 (100) | 87.5 | 166 (100) |
| Group 2 0.5% Test Feed-Added Group | 150 | 5.58 | 109 | 339.27 (113) | 333.69 (113) | 809.3 (103) | 2.43 (91) | 90.8 | 208 (125) |

Survival rate: number of survived chicks after 56 days/(chicks tested − chicks dissected = 120) × 100
( ): values when data of the non-administration group are taken as 100
P.S. (production index): (shipping (56 days old) average body weight × rate of raising) ÷ (shipping day (56 days old) × feed requiring ratio)

EXAMPLE 2

Using 4 groups of broiler chicks (8 days age), each group including 5 chicks, a clostridial infection protection test was carried out during their rearing period in accordance with the procedure of Example 1. The crude drug dried powder-blended feed used in Example 1 (except that the amount of crude drug powders added was changed to 0.5% and 1%) was administered 7 days before the infection. A 1 ml portion of $1\times10^6$ CFU/ml cell suspension of an infectious strain C.P. D-2 was inoculated by forced oral administration, and the chicks were observed for 14 days after the infection. The test schedule is shown in Table 3.

The test results are shown in Tables 4 and 5. As shown in these tables, a significant body weight gain was found in the test substance-administered group. The feed requiring ratio (total feed intake/total body weight) was also improved markedly in the test substance-administered groups 3 and 4 showing respective values of 71 and 70 against the control group 2 taken as 100. No fatality was found in each group.

TABLE 3

Clostridial infection protection test of broilers

| Item | | Days | | | | | | |
| --- | --- | --- | --- | --- | --- | --- | --- | --- |
| | | −7 | −1 | 0 | 3 | 7 | 11 | 14 |
| Treatment | Selection | ○ | ○ | | | | | |
| | Inoculation of Infectious Strain | | | | | | | |
| | Administration of Test Material | ○ | | ←→ | | | | ○ |
| | Anatomic Inspection | | | | | | | ○ |
| Test | Body weight Measure | ○ | ○ | | | | | |
| | Clinical Observation | ○ | | | | | | ○ |
| | Classification of Bacteria | Feces | | | ○ | ○ | ○ | ○ | ○ |
| | | Ileum | | | | | | ○ |
| | | Cecum | | | | | | ○ |

○: performed
A 1 ml portion of $1 \times 10^6$ CFU/ml cell suspension of an infectious strain C.P. D-2 was inoculated by forced oral administration.

TABLE 4

Clostridial infection protection test of broilers

Average body weight and body weight gain in each group

| Test Group | Number of Chicks Tested | Body Weight | | | Body Weight Gain | | |
|---|---|---|---|---|---|---|---|
| | | 7 Days Before Infection | At the Time of Infection | 14 Days After Infection | −7 to 0 | 0 to 14 | −7 to 14 |
| 1 Un-infected Control | 5 | 105 | 203 | 586 | 98 | 383 | 481 |
| 2 Infected Control | 5 | 102 | 199 | 507 | 97 (100) | 308 (100) | 405 (100) |
| 3 Crude Drugs 0.5% Added | 5 | 102 | 219 | 686 | 117 (121) | 467** (152) | 584** (144) |
| 4 Crude Drugs 1.0% Added | 5 | 105 | 222 | 711 | 117 (121) | 489** (159) | 606** (150) |

( ): values when data of the infected control group are taken as 100 (exclude comparisons with the un-infected control group)
*: significant difference by $p < 0.05$ from the infected control group
**: significant difference by $p < 0.01$ from the infected control group

TABLE 5

Feed intake and feed requiring ratio

| Test Group | Number of Chicks Tested | Total Weight Gain (g) | Total Feed Intake (g) | Feed Requiring Ratio (g) |
|---|---|---|---|---|
| 1 Uninfected Control | 5 | 2405 | 7400 | 3.08 |
| 2 Infected Control | 5 | 2025 | 6500 | 3.21 (100) |
| 3 Crude Drugs (0.5% Added) | 5 | 2920 | 6700 | 2.29 (71) |
| 4 Crude Drugs (1.0% Added) | 5 | 3030 | 6800 | 2.24 (70) |

Total body weight gain: total body weight gain from 7 days before the infection until 14 days after the infection
Feed requiring ratio: total feed intake/total body weight gain
( ): values when data of the infected control group are taken as 100 (exclude comparisons with the un-infected control group

EXAMPLE 4

A feed was prepared by mixing 1.0 kg of Cucurbita Seed Coat, 0.5 kg of Plantago Seed (Plantaginis Semen) Powder, 0.3 kg of Lonicera Flower Bud (Jinyinhua or lonicerae flos) Powder and 0.2 kg of Safflower Flower Powder with 0.2 kg of a montmorillonite-based mineral and 7.8 kg of defatted rice bran. These crude drugs were used in the form of dried powders. This feed was mixed with a usual commercial feed in an amount of 0.3% to prepare a test feed.

A total of 2,000 layers (270 to 280 days age) were divided into two groups, and one of the groups was used as a control group reared only with the commercial feed, and the other group was used as a test group with the administration of the test feed.

Tests were carried out twice in different periods. The observation was conducted for 40 days in each test.

In the first test, no layers having abnormal symptoms in the respiratory organ were found in both control and test groups. During this period, dead layers were found 5 in the control group and 1 in the test group. The luster of feather and conditions of combs and dropping were clearly excellent in the test group in comparison with the control group when observed by the naked eye.

The second test was carried out in the same manner as the first test. As the results, similar to the case of the first test, the degree of healthfulness was markedly superior in the test group to that in the control group. During this period, dead layers were found 6 in the control group and 2 in the test group.

EXAMPLE 5

Under the same conditions as the Example 4, 1,000 layers of 220 days age in each of the control and test groups were observed for 140 days. During this period, natural prevail of egg-drop syndrome occurred, but its symptoms were light and recovered quickly in the test group. A total of 14 dead layers were found in the control group, but none in the test group.

EXAMPLE 6

A total of 200 Dekalb breed layers of 220 days age having average body weight of 1,720 g and egg weight of 60.0 g (50% laying, 158 days) were evenly divided into control and test groups. As the rearing conditions, three layers were subjected to group feeding by putting them in a three-step cage of an open pen monitor system and rearing them by full feeding with a nipple waterer. Layers in the control group were fed with a feed for hen use (manufactured by Shimizuminato Shiryo). For use in the test group, the test feed of Example 4 was added to the commercial feed in an amount of 0.5%.

Since the test was carried out under good rearing conditions and when their physiological condition was at the peak in 56 day eggs after the feeding test, abnormality in their health, dead layers, and the like were not found, and the intestinal flora and anatomical findings were good with no differences between the two groups. However, when a taste test of eggs was carried out, deliciousness was found in eggs after 7 days of feeding in the test group.

When the foretaste test was carried out on 18 day eggs by 15 test panelists, the eggs of the test group were superior in all test items as shown in Table 6. Eggs produced after 56 days of the test feed feeding were sent to Japan Food Inspection Center to carry out analyses of whole egg amino acids (18 kinds) and yolk fatty acid composition. With regard to the amino acid composition, sweetness- and deliciousness-related amino acids such as lysine, tyrosine, valine, alanine, proline, glutamic acid, aspartic acid, and the like were found in larger quantities. With regard to the fatty acids, heptadecanoic acid and docosenoic acid which are hardly detectable in chicken egg oil were detected.

TABLE 6

Comparison of tastes of eggs produced by crude drug-fed layers
Taste test (raw eggs)

| Items tested | Control group | Test group |
|---|---|---|
| Absence of avian-specific smell | 0 | 15 |
| Presence of good body | 0 | 10 |
| Light taste | 0 | 5 |
| Presence of sweetness | 0 | 8 |
| Presence of deliciousness | 0 | 15 |

When densities of the yellow yolk pigment were compared using Roche's color fan, color tone of the control group eggs was 9 in minimum and 10 in maximum, while that of the test group eggs was 10 in minimum and 11 in maximum, thus confirming dense yellow tone of the latter.

EXAMPLE 7

Layers were reared using the same feed of Example 6, and forced molting was carried out by fasting when they were 520 days age to examine their resistance to the forced molting as the number of dead layers in control and test groups. Of 1,000 layers, 20 died in the control group, but only 5 in the test group.

EXAMPLE 8

A total of 2,000 Dekalb breed layers were divided evenly into two groups to prepare a control group in which crude drugs were not added and a test plot in which the feed of Example 6 was used (except that the crude drugs were added in an amount of 0.3%). When they reached 380 days age, all layers of the control group started to evacuate greenish feces late in July, their percentage of egg production decreased and some of them became anemic, thus showing likely symptoms of leukocytozoonosis. Accordingly, the control group layers were treated by administration of pyrimethamine. Anatomical findings and blood inspection confirmed leukocytozoonosis. Of 1,000 layers, 26 died. In contrast, all layers of the test group were healthy with no dead case and did not cause leukocytozoonosis even without administration of the antibiotic.

EXAMPLE 9

A feed was prepared by mixing 1.0 kg of Cucurbita Seed Coat, 0.5 kg of Plantago Seed (Plantaginis Semen) Powder, 0.5 kg of Lonicera Flower Bud (Jinyinhua or lonicerae flos) Powder and 0.3 kg of Mabiancao Powder with 0.2 kg of a montmorillonite-based mineral and 7.5 kg of defatted rice bran. This feed was mixed with a commercial feed for quail use (manufactured by Tokai Kigyo) in an amount of 0.5% to prepare a test feed.

A test was carried out with respect to the effect of a feed supplemented with the crude drug powders as active components of the present invention on the egg production and raising of quails.

A total of 2,400 hatched quail chicks of 6.4 g in body weight were divided into a control group in which only the commercial feed was administered and a test group in which the feed of the present invention was administered. Raising area was set to 54 cm² per one chick using a Battery's chick raising cage which was lighted continuously at an illuminance of 10 foot-candela, and water and feed were provided without limitation. Temperature and humidity were controlled at 36° C. and 60% for the first week, 33° C. and 60% for the second week, 28° C. and 50% for the third week and then 25° C. and 40 to 50% for the fourth week and thereafter. The chicks of the control group were transferred into an adult quail cage when they reached 35 days age and 0.2% of an antibiotic additive agent Meiritch 2PX was continuously added to the feed.

Results of this raising test were as follows.

Body weight, survival rate and growing viability showed no significant differences. Though pollution of Newcastle disease occurred at their 46 days age, the number of white eggs (produced by Newcastle disease-infected quails) was 659 in the control group and 505 in the test group, the latter being smaller than the former by a factor of 23.4% which is an advantage from the managing point of view. Reflecting this result, the HI antibody titer of Newcastle disease in their 63 days age was 32 times in average in the control group and 7 times in average in the test group, thus showing smaller degree of pollution in the test group. With regard to the intestinal flora, the number of Clostridium cells at the 30 days age was acceptable value of $10^{-2}$ cells/g in both groups. As shown in Table 7, the number of $E.\ coli$, Staphylococcus and Coccidium cells in the control group were respectively about 10 times, 100 times and about 30 times higher than those in the test group. Unlike the case of the control group, the antibiotic was not used in the test group at the 63 days age, but the intestinal flora was similar to that of the control group.

TABLE 7

Effect of the addition of crude drugs on the behavior of intestinal flora in naturally infected quails

| Age in days | Cells/g | E. coli Control | E. coli Test | Staphylococcus Control | Staphylococcus Test | Coccidium Control | Coccidium Test |
|---|---|---|---|---|---|---|---|
| 30 days | $10^2$ | 0 | 0 | 0 | 3 | 0 | 2 |
| | $10^3$ | 0 | 1 | 1 | 3 | 1 | 5 |
| | $10^4$ | 0 | 4 | 2 | 4 | 3 | 0 |
| | $10^5$ | 4 | 3 | 3 | 0 | 4 | 3 |
| | $10^6$ | 5 | 2 | 3 | 0 | 1 | 0 |
| | $10^7$ | 1 | 0 | 1 | 0 | 1 | 0 |
| 63 days | $10^3$ | | | 0 | 0 | 2 | 2 |
| | $10^4$ | 0 | 0 | 1 | 3 | 6 | 5 |
| | $10^5$ | 0 | 0 | 4 | 6 | 1 | 2 |
| | $10^6$ | 0 | 0 | 2 | 1 | 0 | 1 |
| | $10^7$ | 4 | 5 | 2 | 0 | 0 | 0 |
| | $10^8$ | 5 | 5 | | | | |

EXAMPLE 10

A feed was prepared by mixing 1.0 kg of Cucurbita Seed Coat, 0.5 kg of Plantago Seed (Plantaginis Semen) Powder, 0.3 kg of Lonicera Flower Bud (Jinyinhua or lonicerae flos) Powder and 0.2 kg of Houttuynia Powder with 0.2 kg of a montmorillonite-based mineral and 7.8 kg of defatted rice bran. This feed was added to a commercial feed for piglet in an amount of 0.1% to prepare a feed for piglet.

The thus prepared feed of the present invention was administered to 200 suckling piglets. During the suckling period, about 15% of the piglets were seized with AR (atrophic rhinitis) showing snout deformation as one of the symptoms. However, other symptoms were light and the body weight did not decrease so that they were able to be shipped. During this period, pneumonia, diarrhea, and the like were also found in the pigpen of the control group in which the feed of the present invention was not administered, but these symptoms were not found in the pigpen of the test group in which the feed of the present invention was administered. The pork of piglets raised with the feed of the present invention was free from so-called animal smell and its taste was delicious.

EXAMPLE 11

A feed was prepared by mixing 1.0 kg of Cucurbita Seed Coat, 0.5 kg of Plantago Seed (Plantaginis Semen) Powder, 0.3 kg of Lonicera Flower Bud (Jinyinhua or lonicerae flos) Powder and 0.2 kg of Pugongying Powder with 0.2 kg of a montmorillonite-based mineral and 7.8 kg of defatted rice bran. These crude drugs were used in the form of dried powders. This feed was administered to milking cows in a dose of 50 g/day together with a commercial feed for milking cow. Tests were carried out on 3 milking cows suspected of having breast inflammation of 500,000 to 1,000,000 in the number of somatic cells in milk and 3 milking cows of latent breast inflammation having 1,000,000 or more somatic cells in milk. After 10 days of the feed administration, the number of somatic cells in milk was reduced to 300,000 or less in three of the six milking cows and to 300,000 to 500,000 in the other three.

EXAMPLE 12

When 20 milking cows having an average somatic cells in milk of 660,000 were fed with 50 g/day of the feed of Example 11 together with the commercial feed for milking cow use, the number of somatic cells in milk was reduced to 310,000 and then to 200,000 or less after 10 days and 20 days of the feeding. The number of somatic cells was around 100,000 during the following 4 months but increased to 300,000 when addition of the feed of the present invention was stopped in the fifth month. These results confirmed that generation of breast inflammation was inhibited during administration of the feed of the present invention.

EXAMPLE 13

A feed was prepared by mixing 2.0 kg of Cucurbita Seed Coat with 1.0 kg of Plantago Seed (Plantaginis Semen) Powder, 0.6 kg of Lonicera Flower Bud (Jinyinhua or lonicerae flos) Powder, 1.0 kg of Licorice Powder and 0.4 kg of Juhua Powder. This feed was suspended in 1% volume of feed oil and adsorbed to a commercial assorted feed for yellowtail raising, EP200 (manufactured by Nippon Formula Feed Mfg. Co., Ltd.), thereby obtaining a feed for cultured fish.

Yellowtails having an average body weight of 196 to 197 g were used as the test animal. A total of three groups, each consisting of 500 fishes put into a sea surface crawl of 5 m×5 m×4.5 m in size, were used in each of a control group in which the aforementioned commercial yellowtail raising assorted feed EP200 was administered and a test group in which the feed for cultured fish was administered. The control group included group 1 in which only feed oil was adsorbed to the commercial feed, group 2 in which the above feed for the cultured fish was added in an amount of 0.1% and group 3 in which this feed was added in an amount of 0.2%. As test items, body weight measurement, mucus inspection, parasite inspection and tissue inspection were carried out in the fourth and eighth weeks. A total of 50 fishes in each group were examined.

Results of the raising test were as follows.

The average body weight of 197 g at the time of the start of the test increased to 395 g in the group 1, 405 g in the group 2 and 414 g in the group 3 after 8 weeks of the raising. The group 1 was larger by a factor of 6%, and the group 2 by 9%. The feed requiring ratio, when the value in the group 1 was taken as 100, was low in the group 2 (i.e., 94) and in the group 3 (i.e., 92). The number of a parasite Benedenia seriolae on the body surface was reduced to half in comparison with the number of the control group. The number of Heteraxine heterocerea (gill fluke of yellowtail) was most large at the time of the start of the test in all of the three groups and decreased with the lapse of time. The number of Caligus spinosus doubled after 8 weeks in the group 1 but was almost the same as the initial count in the groups 2 and 3. The amount of mucus on the body surface increased in each group after 4 weeks; 5.6 mg in the group 1, 6.5 mg in the group 2 and 6.2 mg in the group 3. After 8 weeks, the amount decreased in each group; 3.5 mg in the group 1, 4.2 mg in the group 2 and 4.8 mg in the group 3. The amount of lysozyme was most high after 8 weeks; 10.7 mg in the group 1, 14.3 mg in the group 2 and 15.3 mg in the group 3. The number of mucous cells was also the highest in the group 3. Significant findings were not obtained by the pathological and histological inspection of the liver and muscle. Since the addition of the feed of the present invention can increase the body surface mucus as a biological defence mechanism of yellowtail, protection from the invasion of external bacteria, parasites, and the like and increase in the body weight can be expected.

EXAMPLE 14

A test was carried out using cultured Hamachi (young yellowtail) in the same manner as described in Example 13. About 13,000 Mojako (Hamachi fry) having an average body weight of 10.2 g were raised in a crawl of 9 m×9 m×7.5 m in size for 136 days starting on May 18, 1993. During this period, only 2,000 fry were found dead, and this survival rate was markedly superior to those found in the neighbor culture farms. A remarkable finding was that parasitism of Benedenia seriolae was not found. Though parasitism of Heteraxine heterocerca (gill fluke of yellowtail) was observed, it was not a problematic level. The body surface showed no blackish or opaque color.

EXAMPLE 15

Cultured eels were tested. A commercial feed was made into wet mash and 0.1% of the feed of Example 13 was added thereto. A total of 34,500 eel fry having an average body weight of 13 g were used. The survival rate was 99.9%, generation of edwardsiellosis, gill disease and internal and external parasitism were not found, and condition of feed intake and improvement of body weight gain were perfect. The product quality was evaluated refined (taste, aroma) at a raisers' sampling party.

EXAMPLE 16

A 10 kg portion of a feed additive was prepared by mixing 1.0 kg of Cucurbita Seed Coat Powder, 0.5 kg of Plantago Seed Powder, 0.3 kg of Lonicera Flower Powder, 0.2 kg of Safflower Flower Powder, 0.2 kg of a montmorillonite-based mineral and 7.8 kg of defatted rice bran.

This feed additive can be used in the raising of layers by mixing it with other feed for layer.

EXAMPLE 17

A 10 kg portion of a feed additive was prepared by mixing 1.0 kg of Cucurbita Seed Coat Powder, 0.5 kg of Plantago Seed Powder, 0.5 kg of Lonicera Flower Powder, 0.3 kg of Mabiancao Powder, 0.2 kg of a montmorillonite-based mineral and 7.5 kg of defatted rice bran.

This feed additive can be used in the raising of broilers by mixing it with other feed for broiler use.

EXAMPLE 18

A 5 kg portion of a feed additive was prepared by mixing 2.0 kg of Cucurbita Seed Coat Powder, 1.0 kg of Plantago Seed Powder, 0.6 kg of Lonicera Flower Powder and 1.4 kg of Licorice Powder.

This feed additive can be used in the raising of yellowtail, Hamachi, eel, sea bream, and the like by mixing it with other feed for cultured fish.

EXAMPLE 19

Using a broiler breed, tests were carried out in accordance with the procedures of Example 1 and Test Example 1. The mixed feed of Example 1 was used except that it contained Cucurbita Seed Coat Powder, but Plantago Seed Powder, Lonicera Flower Powder and Mabiancao were excluded. Using seeder birds infected with wild coccidium strains *E. acervulina* (attenuated strain) and *E. tenella* (virulent strain), a floor pen test was carried out in accordance with the procedure of Example 1.

Coccidium OPG was measured every week from 7 days to 56 days age. Oocysts were not found until 7 days age. At the age of 14 days, the number of oocysts in average was $0.38 \times 10^4$ in the control group 1 and $0.35 \times 10^4$ in the test group 2 in which 0.5% of the test sample was added. These oocysts seemed to be excreted by the seeder birds. At the age of 21 days, only small type (attenuated strain) oocysts were found in respective amounts of $3.93 \times 10^4$ in the group 1 and $2.84 \times 10^4$ in the group 2. At the age of 28 days, small type oocysts were $29.02 \times 10^4$ and medium type (virulent strain) oocysts were $3.76 \times 10^4$ in the group 1, and small type oocysts were $4.46 \times 10^4$ and medium type oocysts were $1.27 \times 10^4$ in the group 2. Accordingly, the small type and medium type oocysts excreted in the group 1 were 6.5 times and 2.9 times larger than those of the group 2. At the age of 35 days, excretion of oocysts was reduced in both groups, and slight excretion of oocysts was found after 42 days or more of age only in the group 1 and not in the group 2. At the age of 56 days, $0.04 \times 10^4$ and $0.17 \times 10^4$ small and medium type oocysts were found in the group 1, but they were not found in the group 2. A significant difference was found between these two groups.

Throughout the tested period, coccidium was found in the intestinal tract, and dead chicks were found 11 in the group 1 and 5 in the group 2. Bloody stool was found in 150 chicks in the group 1 and 18 in the group 2.

EXAMPLE 20

In accordance with Example 13, two groups of yellowtails (initial average body weight, 200 g), each consisting of 500 fishes put into a sea surface crawl of 5 m×5 m×4.5 m in size, were prepared. The feed was prepared by adding 0.5% of Cucurbita Seed Coat Powder to the commercial yellowtail raising assorted feed EP200. In this case, the crude drugs Plantago Seed Powder, Lonicera Flower Bud Powder, Licorice Powder and Juhua Powder used in Example 13 were excluded from the above feed. On the first day and the fourth and eighth weeks, 10 fishes in each group were subjected to parasite inspection. The number of parasites on the body surface in the drug-added group was reduced to half in comparison with the number of the control group. The number of *Heteraxine heterocerca* (gill fluke of yellowtail) was most high in both groups when the test was started and decreased with the lapse of time. The number of *Caligus spinosus* doubled after 8 weeks in the control group 1 but was almost the same as the initial count in the group 2.

EXAMPLE 21

A test was carried out using cultured Hamachi (young yellowtail) in the same manner as described in Examples 13 and 14. About 10,000 Mojako (Hamachi fry) having an average body weight of 10.4 g were raised in a crawl of 9 m×9 m×7.5 m in size for 136 days. During this period, only 1,800 fry were found dead, and this survival rate was markedly superior to those found in the neighbor culture farms. A remarkable finding was that parasitism of *Benedenia seriolae* was not found. Though parasitism of gill fluke of yellowtail was observed, it was not a problematic level.

Effect of the Invention

The crude drug-compounded feed of the present invention comprises at least one (preferably all three) of Cucurbita Seed, Plantago and Lonicera as fundamental components and, if desired, further comprises Safflower for egg-producing chicken, Mabiancao for broilers, Houttuynia for swine, Pugongying for cattle, or Juhua and Licorice for fish (dried powders). By adding it to a marketed feed in an amount of 0.1 to 0.5%, the economical loss especially due to the natural infection with parasites, bacteria and viruses is prevented, the biological protection is strengthened, and the meat quality and egg quality can be improved. In addition, body weight gain, feed requiring ratio, feed requiring rate, and the like are improved. Combined use of these crude drugs enables the protection against a broad range of microorganisms in comparison with single use, and potent synergic effects were observed in the combined use. Particularly excellent effects were observed against opportunistic infections which are increasing these days.

What is claimed is:

1. A feed comprising three crude drugs of Cucurbia Seed in the amount of at least 0.01% by weight, Plantago in an amount of at least 0.005% by weight and Lonicera in an amount of at least 0.003% by weight, all based on the weight of the feed, and at least one additional crude drug selected from the group consisting of Safflower, Licorice, Mabiacao, Pugongying, Houttuynia and Juhua.

2. A feed comprising three crude drugs of Cucurbita Seed in an amount of at least 0.01% by weight, Plantago in an amount of at least 0.005% by weight and Lonicera in an amount of at least 0.003% by weight, all based on the weight of the feed.

3. A method of treating animals, fowl and fish to increase their resistance to disease, which comprises administering to the animals, fowl and fish a disease resistant amount of the feed of claim 1.

* * * * *